(12) United States Patent
Janik et al.

(10) Patent No.: US 10,960,127 B2
(45) Date of Patent: Mar. 30, 2021

(54) APPARATUS AND METHOD FOR MEASURING RECIRCULATION

(71) Applicant: B. BRAUN AVITUM AG, Melsungen (DE)

(72) Inventors: Waldemar Janik, Melsungen (DE); Silvie Krause, Melsungen (DE)

(73) Assignee: B. BRAUN AVITUM AG, Melsungen (DE)

( * ) Notice: Subject to any disclaimer, the term of this patent is extended or adjusted under 35 U.S.C. 154(b) by 471 days.

(21) Appl. No.: 15/727,114

(22) Filed: Oct. 6, 2017

(65) Prior Publication Data
US 2018/0099081 A1 Apr. 12, 2018

(30) Foreign Application Priority Data
Oct. 10, 2016 (DE) .................. 10 2016 119 259.7

(51) Int. Cl.
*A61M 1/36* (2006.01)
*A61M 1/14* (2006.01)

(52) U.S. Cl.
CPC ........... *A61M 1/3658* (2014.02); *A61M 1/14* (2013.01); *A61M 1/3609* (2014.02);
(Continued)

(58) Field of Classification Search
CPC .... A61M 1/3658; A61M 1/3609; A61M 1/14; A61M 2205/3368; A61M 2205/36; A61M 2205/3673
See application file for complete search history.

(56) References Cited

U.S. PATENT DOCUMENTS 5,588,959 A * 12/1996 Ahmad ............... A61M 1/3653 604/28
5,685,989 A * 11/1997 Krivitski ............. A61M 1/3653 210/103

(Continued)

FOREIGN PATENT DOCUMENTS

DE 19528907 C1 11/1996
DE 19702441 C1 * 2/1998 .......... A61M 1/1607
(Continued)

OTHER PUBLICATIONS

Extended European Search Report for European Application No. 17105541.2, dated Mar. 1, 2018 with translation, 15 pages.
(Continued)

*Primary Examiner* — Philip R Wiest

(57) ABSTRACT

An apparatus for measuring recirculation using thermodilution during extracorporeal blood treatment including a temperature varying unit arranged to cyclically heat and/or cool blood in a venous tube segment of the blood tube system for a quasi-continuous recirculation measurement; and a detecting device configured to measure a variation of a physical parameter resulting from the heating and/or cooling. The detecting device is arranged to detect, in a case free from recirculation, a first physical parameter and to detect, in a case afflicted with recirculation, a physical parameter varied by the cooling and/or heating of the blood by the temperature varying unit as a second physical parameter in the blood tube system. A method for measuring recirculation carries out appropriate steps.

12 Claims, 1 Drawing Sheet

(52) U.S. Cl.
CPC . *A61M 2205/3368* (2013.01); *A61M 2205/36* (2013.01); *A61M 2205/3673* (2013.01)

(56) References Cited

U.S. PATENT DOCUMENTS

| | | | | |
|---|---|---|---|---|
| 5,830,365 | A * | 11/1998 | Schneditz | A61M 1/3621 210/739 |
| 6,626,857 | B1 * | 9/2003 | Ohta | A61M 1/3455 422/44 |
| 9,370,614 | B2 | 6/2016 | Ahrens | |
| 2005/0131332 | A1 * | 6/2005 | Kelly | A61M 1/341 604/4.01 |
| 2006/0254982 | A1 * | 11/2006 | Kopperschmidt | A61M 1/361 210/646 |
| 2008/0015487 | A1 * | 1/2008 | Szamosfalvi | A61M 1/3658 604/6.07 |
| 2008/0031773 | A1 * | 2/2008 | Eccleston | A61M 1/3666 422/44 |
| 2009/0221948 | A1 * | 9/2009 | Szamosfalvi | A61M 1/3458 604/6.07 |
| 2010/0276367 | A1 * | 11/2010 | Zhang | A61M 1/3658 210/647 |
| 2011/0004141 | A1 * | 1/2011 | Zhang | A61M 1/1617 604/6.09 |
| 2011/0309019 | A1 * | 12/2011 | Ahrens | G01J 3/0286 210/645 |
| 2013/0303964 | A1 * | 11/2013 | Kopperschmidt | A61M 1/14 604/6.11 |
| 2014/0083943 | A1 * | 3/2014 | Nuernberger | A61M 1/1656 210/646 |
| 2014/0291534 | A1 * | 10/2014 | Ahrens | A61M 1/1694 250/373 |
| 2015/0034557 | A1 * | 2/2015 | Pouchoulin | A61M 1/1601 210/646 |
| 2015/0150715 | A1 * | 6/2015 | Svitek | A61M 1/369 422/46 |

FOREIGN PATENT DOCUMENTS

| | | |
|---|---|---|
| DE | 19702441 C1 | 2/1998 |
| DE | 102010015664 A1 | 10/2011 |
| DE | 102013103222 A1 | 10/2014 |
| EP | 1970080 A1 | 9/2008 |
| WO | 2009065611 A1 | 5/2009 |
| WO | 2017140424 A2 | 8/2017 |

OTHER PUBLICATIONS

German Search Report for German Application No. 10 2016 119 259.7, with partial translation, dated May 8, 2017—16 Pages.

* cited by examiner

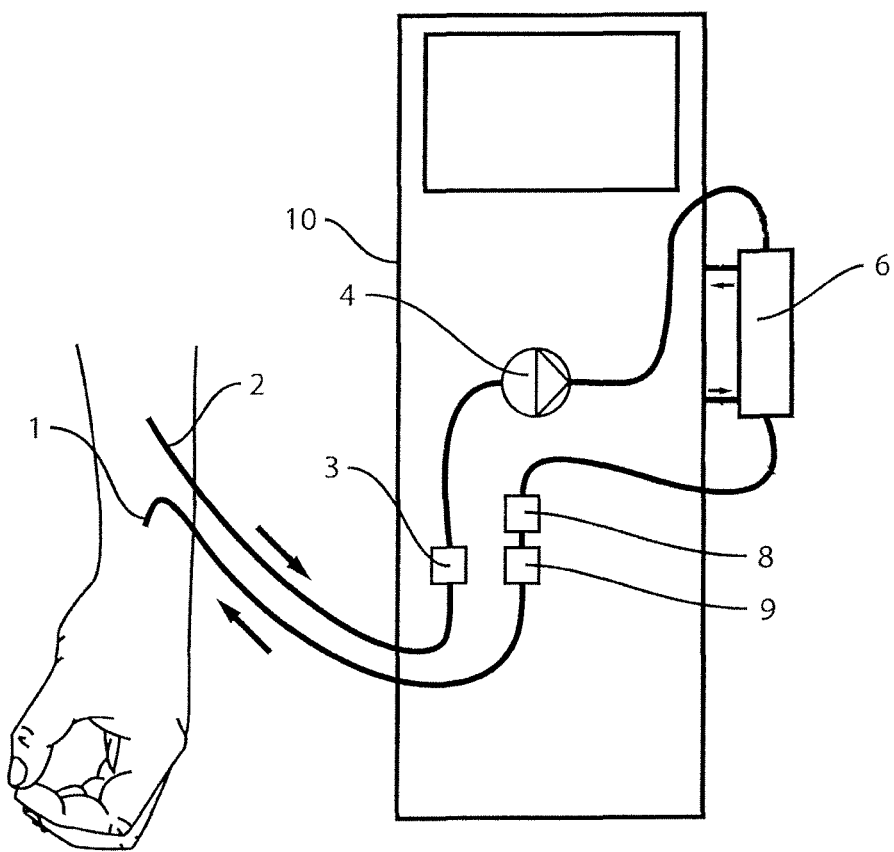

APPARATUS AND METHOD FOR MEASURING RECIRCULATION

CROSS REFERENCE TO RELATED APPLICATIONS

This application claims priority to German application DE 10 2016 119 259.7 filed Oct. 10, 2016, the contents of such application being incorporated by reference herein.

FIELD OF THE INVENTION

The invention relates to an apparatus and a method for quasi-continuous recirculation measurement through thermodilution and especially relates to an apparatus and a method for measuring recirculation through thermodilution during extracorporeal blood treatment allowing for an at least quasi-continuous detection of recirculation in a blood tube system of an extracorporeal blood circulation during extracorporeal blood treatment.

BACKGROUND OF THE INVENTION

In known methods for extracorporeal blood treatment or else blood purification, such as, for example, hemodialysis, hemofiltration and hemodiafiltration, a patient's blood is guided through an extracorporeal circulation. Usually a so-called shunt is inserted in the patient to form an access to the vascular system. In this case, a shunt is an arteriovenous connection in the forearm which can also be realized with an implant. For a dialysis treatment, the shunt is usually punctured by two syringes. Via the one syringe, the blood is guided from the patient for purification to the dialyzer. Via the second syringe, the purified blood is returned to the patient. If the blood flow in the extracorporeal circulation exceeds the blood flow in the shunt of the patient, this is resulting in recirculation during which part of the already purified blood is repeatedly guided from the shunt to the dialyzer. Reasons for this may be syringes that are not optimally inserted or stenoses in the shunt.

Therefore, the occurrence of a recirculation may serve for predicting an access failure, more exactly speaking may serve as a late predictor or a late basis of prediction. Since (shunt) recirculations usually are detrimentally accompanied by reduction of efficiency of the dialysis treatment, in the short run dialysis free from recirculation can be provided, to be sure. However, substantially occurrence of recirculation may be considered in favor of a better diagnosis of the shunt and, where necessary, an as quick initiation of revision as possible, as determinations of recirculation over a quite long period of time are capable of providing information about the condition of the shunt.

Known measures in the case of determinations of recirculation involve heating of a dialysate, for example a dialysate passing through a dialyzer, measuring of a temperature bolus and, respectively, a conductivity bolus at the dialysate outlet of a dialyzer after varying a physical or chemical parameter at the dialysate inlet, or apparatuses which require temperature sensors both in an arterial circulation segment and in a venous circulation segment. The size of the volume involved in the known measures, such as that of the dialysate, entails slow variations of a parameter considered in each case, however, and, as a consequence, inert system reactions which permit measurements at long time intervals only.

Said known measures thus are not adapted to provide any measuring values in quick or short time sequence and therefore are not suited for continuous or quasi-continuous measurement. So far, continuous or at least quasi-continuous measurements or the determination of an optimum blood flow on the basis of recirculation determination measurements performed continuously or quasi-continuously are not possible.

SUMMARY OF THE INVENTION

Therefore, an object underlying the invention is to provide an apparatus and a method for a recirculation measurement which can be repeatedly performed easily and cyclically at a short time sequence.

Moreover, the invention is intended to enable finding an optimum blood flow in which just no recirculation is occurring, wherein such optimum blood flow shall be adapted to be equally quasi-continuously determined and adjusted even during therapy.

In accordance with the invention, this object is achieved by an apparatus comprising the features of the independent claim and by a method as defined in the claims.

Advantageous developments of the invention are the subject matter of the dependent claims.

In conformity with an inventive idea, the invention focuses on providing an apparatus for a recirculation measurement to be easily performed which carries out recirculation measurements which are repeatable especially at a short time sequence, i.e. continuous and at least quasi-continuous, thus enabling quick possibilities of reacting to a change of condition of a patient, for example due to circulation stress during treatment. Moreover, by the apparatus and a clever procedural realization the optimum blood flow during which just no recirculation takes place can be automatically found. Said blood flow then can be determined and adjusted equally quasi-continuously during therapy.

By cyclic variation of a relevant physical parameter, for example cyclic variation (increasing/reducing) the blood temperature in the venous part of the blood tube segment, and measurement of the physical parameter, for example of the temperature in the arterial segment, on the one hand the access recirculation can be determined and, on the other hand, the optimum blood flow during which no recirculation will occur can be determined and adjusted. The variation of the physical parameter, for example the temperature variation, may be carried out with (at least) one Peltier element, for example. When the cyclic variation is carried out at a short time sequence, this will result in a continuous and at least quasi-continuous measurement.

According to aspects of the invention, advantageously no variations of any other setting parameters such as e.g. dialysate and blood flow are necessary, simple and quick recirculation measurement will be possible due to reduced inertia by reduced dead times, measuring operations are repeatable in favor of continuous measurement, no infusion solutions are necessary, optimum blood flow can be automatically established and the blood flow can be automatically adapted in terms of control, and monitoring of the optimum blood flow and thus shunt flow monitoring and, respectively, shunt monitoring are possible.

Furthermore, recirculation with advanced treatment time usually points to instable circulation so that detection can be utilized as a trigger event for a biofeedback system by which then, for example, blood pressure measurement can be carried out and/or an ultrafiltration rate is rendered to be adaptable or the composition of the dialysate is rendered to be adaptable.

In detail, an object is achieved by an apparatus for measuring recirculation through thermodilution during extracorporeal blood treatment, comprising a temperature varying unit which is arranged to cyclically heat or cool blood in a venous tube segment of the blood tube system for an at least quasi-continuous recirculation measurement; and a detecting device which is configured to measure a variation of a physical parameter resulting from heating or cooling of the blood in an arterial tube segment of the blood tube system, the detecting device being arranged to detect, in a case free from recirculation in which during extracorporeal blood treatment no recirculation of venous blood into arterial blood is occurring, a first physical parameter and to detect, in a case afflicted with recirculation in which during extracorporeal blood treatment recirculation of venous blood into arterial blood is occurring, a physical parameter varied by cooling or heating of the blood in the venous tube segment by the temperature varying unit as a second physical parameter in the blood tube system.

The preferred temperature range, in which the blood can be cooled and/or heated or which is suitable for the recirculation measurement according to aspects of the invention, is between 30° C. and 41° C. (including 30° C. and 41° C.).

Preferably, in such apparatus a pump is arranged to pump blood in a blood tube system of an extracorporeal blood circulation and/or the temperature varying unit is arranged downstream of a blood outlet of a dialyzer and/or a temperature detecting unit is provided and arranged to detect the temperature of the blood at or in the venous tube segment.

Preferably, the temperature varying unit is a Peltier element.

Preferably, the physical parameter which varies along with the change in temperature by the temperature varying unit, a temperature of the blood assigned to an arterial blood temperature, a pressure or a power.

Preferably, the apparatus is arranged to generate a temperature signal curve in at least one temperature detecting unit by cyclic heating and cooling of the blood in the venous tube portion, wherein amplitudes of the temperature signal curve and/or areas below the temperature signal curve can be evaluated for quasi-continuous determination of a recirculation.

Preferably, in the apparatus recirculation can be determined by a quantitative index and/or a qualitative parameter relating to medical relevance of the recirculation, wherein the qualitative parameter can be output by way of a percentage threshold "recirculation equal to or more than X percent" with X being a numerical percentage.

Preferably, the pump can be controlled, depending on a parameter variation detected by the detecting unit, to adjust optimum blood flow for a dialysis treatment.

Preferably, the pump can be controlled, upon detection of a parameter variation at the detecting unit on the basis of which occurrence of recirculation is determined, to reduce the blood flow until a parameter variation is detected at the detecting unit on the basis of which disappearance of the recirculation is determined, wherein the blood flow at which recirculation disappears is adjusted as an optimum blood flow.

Preferably, the apparatus is arranged to determine occurrence of recirculation upon detection of a first parameter variation at the detecting unit and to determine disappearance of recirculation upon detection of a second parameter variation at the detecting unit, to combine a first blood flow during the first parameter variation and a second blood flow during the second parameter variation mathematically into a resulting blood flow and to control the pump for adjusting the resulting blood flow as an optimum blood flow.

In accordance with the invention, an object is also achieved by a method for recirculation measurement through thermodilution during extracorporeal blood treatment using the apparatus according to any one of the preceding claims, comprising the steps of: heating or cooling blood in a venous tube segment of a blood tube system with the temperature varying unit; and measuring a variation of a physical parameter resulting from the heating and/or cooling of the blood in an arterial tube segment of the blood tube system with the detecting unit, wherein, in a case free from recirculation in which during extracorporeal blood treatment no recirculation of venous blood to arterial blood is occurring, a first physical parameter is detected and, in a case afflicted with recirculation in which during extracorporeal blood treatment recirculation of venous blood into arterial blood is occurring, a physical parameter varied by the cooling or heating of the blood in the venous tube segment by the temperature varying unit is detected as a second physical parameter in the blood tube system.

BRIEF DESCRIPTION OF THE DRAWING

The invention is best understood from the following detailed description when read in connection with the accompanying drawing. Included in the drawing is the following FIGURE:

FIG. 1 illustrates a schematic configuration of the apparatus for measuring recirculation through thermodilution during extracorporeal blood treatment according to an embodiment in which the temperature is used by way of example as a relevant physical variable or relevant parameter. However, the invention is not restricted to the temperature as a relevant physical variable or relevant parameter. In specific applications, numerous physical variables and parameters are possible as long as the cyclic variation thereof at a short time sequence permits an at least quasi-continuous measurement for establishing occurring recirculation, such as e.g. a pressure or a force.

DETAILED DESCRIPTION OF THE PREFERRED EMBODIMENTS

In detail, FIG. 1 shows in a schematic indication a patient from whom blood is collected at an arterial access 2 with a pump 4, in this embodiment a blood pump in a dialysis apparatus 10, for example, via a blood tube system. Between the arterial access 2 at the patient and the pump 4 a temperature adapted to be assigned to the arterial blood temperature is measured at an arterial tube portion of the blood tube system by a detecting unit 3 which may be a sensor suited for temperature detection or temperature measurement, for example. The collected blood is guided through a dialyzer 6 for purifying the same. Downstream of a blood outlet of the dialyzer 6, a or a first temperature variation unit 8 is arranged which may be, for example, a heating/cooling element of the Peltier element type in the present embodiment. Peltier elements offer the advantage that they can be used for heating and cooling by reversing the polarity of the supply voltage. However, the temperature varying unit 8 is not limited to Peltier elements. The temperature varying unit 8 heats or cools the blood in the venous tube segment of the blood tube system downstream of the dialyzer 6. Another or second temperature detecting unit 9 which may equally be a sensor suited for temperature detection or temperature measurement and may be provided as a safety device for identifying excessive cooling or heating by the temperature varying unit 8 as quickly as possible, may be arranged in the venous tube segment of the blood tube system and detect the temperature at or in the venous tube segment.

For establishing or determining recirculation, the apparatus varies the temperature of the venous blood with the temperature varying unit 8. When afflicted with recirculation, i.e. upon occurrence of recirculation, part of the venous blood repeatedly flows, together with the arterial blood, through the arterial tube segment, thus rendering a change in temperature detectable at the detecting device 3 due to the varied temperature of the venous blood portion. When being free from recirculation, i.e. when no recirculation is present, the temperature at the detecting device 3 remains unchanged. In this way, by cyclic heating and cooling with the temperature varying unit 8 recirculation can be determined quasi-continuously. For evaluation, for example, the amplitudes of temperature signal curves or areas below such curves generated at the detecting device 3 can be utilized. Recirculation can be output both as a quantitative index and in terms of quality. In terms of quality may mean in this embodiment that by way of a percentage value based on the freedom from recirculation, for example, it is indicated whether or not medically relevant recirculation (for example recirculation >15%) is given. It is understood that the percentage value or a threshold value for fixing the same is not limited to the afore-mentioned concrete value.

In a modification, the afore-described apparatus and a corresponding method can be used for establishing or determining and/or adjusting an optimum blood flow for a dialysis treatment.

For this purpose, for example upon connecting the patient at the beginning of dialysis treatment when the (initial) blood flow as a standard is lower than the blood flow during the remaining duration of treatment, the arterial temperature can be measured at the detecting device 3. By the temperature varying unit 8 venous blood returning to the patient via an access 1 then is cooled or heated by a predetermined temperature difference and the blood flow generated by the pump 4 then is gradually increased. When a temperature variation is detected at the detecting device 3, presence of a recirculation is determined. In this case, the blood flow in the blood tube system exceeds the shunt flow, i.e. the blood flow through the shunt, in the patient's arm and thus is selected to be too high.

Due to sufficiently short dead times, the blood flow at the time of detecting the occurrence of recirculation may be considered to be an optimum blood flow. An even more accurate value can be obtained when dead times are known or can at least be assessed in numbers and said blood flow considered to be optimal is reduced by a predetermined value with consideration of the dead times.

Alternatively, the blood flow can be slowly reduced after detecting the occurrence of recirculation until no further recirculation is determined, i.e. until the recirculation disappears. In this alternative, the blood flow upon disappearance of recirculation may be considered to be the optimum blood flow.

Alternatively or additionally, it is possible to average the blood flow upon detection of the occurrence of recirculation and to average the blood flow upon disappearance of recirculation, i.e. to form a mean value from corresponding blood flow values, or to mathematically combine them into a resulting blood flow in a different suitable manner. In this case, the resulting blood flow corresponds to the optimum blood flow.

Moreover, the optimum blood flow can be automatically or manually established and/or adjusted, wherein manually in this embodiment means that a user manually increases the blood flow generated by the pump 4 until the occurrence of recirculation is detected and subsequently manually reduces the same, where necessary.

It is understood that establishing the optimum blood flow is not limited to the beginning of a dialysis treatment. The optimum blood flow may also be established during dialysis treatment, for example upon request by the user or automatically, when or while the temperature varying unit 8 cyclically heats and cools the blood in the venous tube portion. Furthermore, it is also possible to quasi-continuously determine the optimum blood flow. In this way, the blood flow can be tracked with the pump 4.

In another modification, the apparatus and the method according to the embodiment permit a short-term, medium-term and/or long-term trend analysis of the optimum blood flow. Accordingly, for each therapy a characteristic combination of values is established. This may be, for example, the median of all blood flows established during treatment in combination with the range of all blood flows. An average blood flow value including the standard deviation or other adequate combinations of the descriptive statistics can be realized as well. The characteristic combinations of values can be stored on a patient's card, a data management system or directly on/in the dialysis apparatus 10. The characteristic combinations of values can be applied over time. The derivation of the data after time allows concluding variations at the shunt vessel, as the derivation becomes negative when the optimum blood flow and thus also the shunt flow are decreasing over time. For short-term trend analyses, preferably at least two or optimally three treatments are considered, for medium-term analyses at least three to nine treatments are considered and for long-term analyses at least ten treatments are considered. In this way, the dialysis apparatus 10 including the apparatus according to the embodiment can output warnings by way of the trend established when a negative derivation indicates deterioration of the shunt (not shown) so that medical staff members can take further diagnostic measures, when required.

As afore-described, in an apparatus for measuring recirculation with thermodilution in the case of extracorporeal blood treatment a temperature varying unit 8, for example a Peltier element, is arranged to cyclically heat and/or cool blood in a venous tube segment of the blood tube system for quasi-continuous recirculation measurement, and a detecting device 3, which may be a temperature sensor, a pressure sensor or a force sensor, for example, is configured to measure a physical variable, for instance a temperature of the blood assigned to an arterial blood temperature, in an arterial tube segment of the blood tube system. In a case in which during extracorporeal blood treatment no recirculation from venous blood into arterial blood is occurring, the detecting device 3 detecting the physical variable detects a first physical variable relating to arterial blood in this case, wherein the first physical variable remains unchanged between individual measurements. In a case afflicted with recirculation in which during extracorporeal blood treatment a recirculation of blood from the venous tube portion into arterial blood occurs and the blood from the venous tube portion varied with respect to the physical parameter varied along with the temperature variation by the temperature varying unit 8 causes a parameter variation input or a parameter variation output into or out of the arterial blood, the detecting device 3 detects a physical parameter varied by the cooling or heating of the blood in the venous tube segment by the temperature varying unit 8 as a second physical parameter of the blood in the blood tube system.

A pump 4 which in the form of a blood pump is arranged for pumping blood in a blood tube system of an extracorporeal blood circulation ensures blood circulation inside the blood tube system.

The temperature varying unit 8 may be arranged downstream of a blood outlet of a dialyzer 6. Furthermore, a temperature detecting unit 9 may be provided in the area of the venous tube segment, for example for control and/or detection purposes, and may be arranged to detect the temperature of the blood at or in the venous tube segment.

The temperature varying unit 8 preferably is a Peltier element which by reversing the polarity of its supply voltage can be cyclically changed alternately between a heat-generating operation and a cooling operation and thus can be operated for cyclically heating and/or cooling the blood in the venous tube portion. In this way, at least a quasi-continuous recirculation measurement having short dead times, i.e. quick reaction or response time with a rapid cycle sequence, can be achieved.

During cyclic heating and cooling of the blood in the venous tube portion, according to the embodiment a temperature signal curve can be generated at the detecting device 3 in this case detecting a temperature, with the amplitudes and/or areas below the curve thereof being adapted to be evaluated for quasi-continuous determination of recirculation.

Within the scope of evaluation, recirculation can be determined by e.g. a quantitative index and/or a qualitative variable with respect to medical relevance of recirculation. The qualitative variable may be output as a percentage value or threshold value "recirculation equal to or higher than X percent" based on the case free from recirculation with X being a numerical percentage.

Furthermore, the pump 4 may be controllable in response to a variation of the physical parameter detected at the detecting device 3 to adjust an optimum blood flow for a dialysis treatment. More exactly speaking, the pump 4 may be controllable, upon detection of a variation of parameter at the detecting device 3 on the basis of which occurrence of recirculation is determined, to reduce the blood flow until a variation of the parameter is detected at the detecting device 3 on the basis of which the disappearance of recirculation is determined, with the blood flow at which recirculation disappears being adjusted as optimum blood flow.

Alternatively, occurrence or appearance of recirculation can be determined upon detection of a first variation of a physical parameter at the detecting device 3, and disappearance of recirculation can be determined upon detection of a second variation of a physical parameter at the detecting device 3, a first blood flow during the first variation of parameter and a second blood flow during the second variation of parameter may be mathematically combined into a resulting blood flow, and on this basis, the pump 4 may be controlled to adjust the resulting blood flow as an optimum blood flow.

In the foregoing, the invention has been described by way of a preferred embodiment. It is understood that details of the described preferred embodiment do not limit the invention as such and in a way obvious to those skilled in the art various changes, modifications and/or equivalents may be resulting all of which as such are within the protective scope of the invention defined by the attached claims.

It is especially understood that, for the case of a physical parameter other than the temperature, those skilled in the art will easily come across components equivalent or corresponding to the components appropriately related to temperature according to the embodiment which are suited for detecting and processing the other physical parameter and can be configured for this purpose.

The invention claimed is:

1. An apparatus for measuring recirculation through thermodilution during extracorporeal blood treatment, comprising:
    a detecting device configured to repeatedly measure a variation of blood temperature resulting from heating and/or cooling of blood in an arterial tube segment of a blood tube system and provide at least quasi-continuous recirculation measurement; and
    a temperature varying unit arranged in a venous tube segment of the blood tube system, the temperature varying unit configured to cyclically alternate between a heating operation and a cooling operation to cyclically heat and cool blood in the venous tube segment and generate a temperature signal curve at the detecting device for said at least quasi-continuous recirculation measurement,
    wherein the detecting device is arranged to detect blood temperature in a case free from recirculation in which no recirculation of venous blood into arterial blood is occurring during extracorporeal blood treatment, and to detect blood temperature in a case afflicted with recirculation in which recirculation of venous blood into arterial blood is occurring during extracorporeal blood treatment, said blood temperature being varied by cyclical heating and cooling of the blood in the venous tube segment by the temperature varying unit.

2. The apparatus according to claim 1, wherein a pump is arranged to pump blood in the blood tube system of an extracorporeal blood circulation.

3. The apparatus according to claim 2, wherein the pump can be controlled in response to the variation of blood temperature detected at the detecting device to adjust optimum blood flow for a dialysis treatment.

4. The apparatus according to claim 3, wherein the pump is controllable to reduce the blood flow, upon detection of the variation of blood temperature at the detecting device on the basis of which the occurrence of recirculation is determined, until the variation of blood temperature is detected at the detecting device on the basis of which the disappearance of recirculation is determined, with the blood flow in which recirculation disappears being adjusted as an optimum blood flow.

5. The apparatus according to claim 3, the apparatus configured to determine occurrence of recirculation upon detection of a first variation of blood temperature at the detecting device and to determine disappearance of recirculation upon detection of a second variation of blood temperature at the detecting device, to mathematically combine a first blood flow upon the first variation of blood temperature and a second blood flow upon the second variation of blood temperature into a resulting blood flow and to control the pump so as to adjust the resulting blood flow as an optimum blood flow.

6. The apparatus according to claim 1, wherein the temperature varying unit is arranged downstream of a blood outlet of a dialyzer.

7. The apparatus according to claim 1, wherein a temperature detecting unit is provided and arranged to detect the temperature of the blood at or in the venous tube segment.

8. The apparatus according to claim 1, wherein the temperature varying unit is a Peltier element.

9. The apparatus according to claim 1 wherein the apparatus is configured to evaluate amplitudes of and/or areas below the temperature signal curve for the at least quasi-continuous recirculation measurement.

10. The apparatus according to claim 1, wherein a recirculation can be determined by a quantitative index and/or a qualitative variable with respect to medical relevance of recirculation, wherein the qualitative variable can be output by way of a percentage threshold "recirculation equal to or larger than X percent" with X being a numerical percentage.

11. A method of measuring recirculation through thermodilution during extracorporeal blood treatment, the method comprising the steps of:
cyclically alternating a temperature varying unit between a heating operation and a cooling operation to cyclically heat and cool blood in a venous tube segment of a blood tube system and generate a temperature signal curve at a detecting device; and
repeatedly measuring a change of blood temperature resulting from cyclical heating and cooling of the blood in an arterial tube segment of the blood tube system by the detecting device to provide at least quasi-continuous recirculation measurement;
wherein in a case free from recirculation in which during extracorporeal blood treatment no recirculation of venous blood into arterial blood is occurring, blood temperature is detected and, in a case afflicted with recirculation in which during extracorporeal blood treatment recirculation of venous blood into arterial blood is occurring, blood temperature varied by cyclical heating and cooling of the blood in the venous tube segment by the temperature varying unit is detected.

12. An apparatus for measuring recirculation through thermodilution during extracorporeal blood treatment, comprising:
a detecting device configured to repeatedly measure a variation of blood temperature resulting from heating and/or cooling of blood in an arterial tube segment of a blood tube system and provide at least quasi-continuous recirculation measurement;
a temperature varying unit arranged in a venous tube segment of the blood tube system, the temperature varying unit configured to cyclically alternate between a heating operation and a cooling operation to cyclically heat and cool blood in the venous tube segment and generate a temperature signal curve at the detecting device for said at least quasi-continuous recirculation measurement; and
a pump configured to pump blood in the blood tube system of an extracorporeal blood circulation,
wherein the detecting device is arranged to detect blood temperature in a case free from recirculation in which no recirculation of venous blood into arterial blood is occurring during extracorporeal blood treatment, and to detect blood temperature in a case afflicted with recirculation in which recirculation of venous blood into arterial blood is occurring during extracorporeal blood treatment, the blood temperature being varied by the cyclical heating and cooling of the blood in the venous tube segment by the temperature varying unit,
wherein the pump is configured to be controlled in response to variation of blood temperature detected at the detecting device to adjust optimum blood flow for a dialysis treatment, and
wherein the apparatus is configured to determine occurrence of recirculation upon detection of a first variation of blood temperature at the detecting device and to determine disappearance of recirculation upon detection of a second variation of blood temperature at the detecting device, to mathematically combine a first blood flow upon the first variation of blood temperature and a second blood flow upon the second variation of blood temperature into a resulting blood flow and to control the pump so as to adjust the resulting blood flow as an optimum blood flow.

* * * * *